United States Patent
Umebayashi (10) Patent No.: US 8,821,360 B2
(45) Date of Patent: Sep. 2, 2014

(54) METHOD FOR MANUFACTURING DISPOSABLE WORN ARTICLE, AND MANUFACTURING APPARATUS THEREFOR

(75) Inventor: Toyoshi Umebayashi, Osaka (JP)

(73) Assignee: Zuiko Corporation, Osaka (JP)

( * ) Notice: Subject to any disclaimer, the term of this patent is extended or adjusted under 35 U.S.C. 154(b) by 571 days.

(21) Appl. No.: 13/146,736

(22) PCT Filed: Jan. 22, 2010

(86) PCT No.: PCT/JP2010/000351
§ 371 (c)(1),
(2), (4) Date: Jul. 28, 2011

(87) PCT Pub. No.: WO2010/089964
PCT Pub. Date: Aug. 12, 2010

(65) Prior Publication Data
US 2011/0287919 A1 Nov. 24, 2011

(30) Foreign Application Priority Data
Feb. 3, 2009 (JP) .................................. 2009-022293

(51) Int. Cl.
*B65H 45/04* (2006.01)
(52) U.S. Cl.
USPC .......................................... 493/424; 493/405
(58) Field of Classification Search
USPC .......................................... 493/405, 409, 424
IPC ............ A61F 13/15,13/56, 13/49; B65H 45/04, B65H 45/00; B65B 63/045
See application file for complete search history.

(56) References Cited

U.S. PATENT DOCUMENTS

| | | | |
|---|---|---|---|
| 3,782,714 A * | 1/1974 | Spencer et al. | 493/250 |
| 5,779,831 A * | 7/1998 | Schmitz | 156/73.1 |
| 5,788,805 A | 8/1998 | Herrmann | |
| 6,582,543 B1 | 6/2003 | Nilsson et al. | |
| 6,702,798 B2 * | 3/2004 | Christoffel et al. | 604/385.201 |
| 7,322,925 B2 * | 1/2008 | Couillard et al. | 493/450 |
| 7,335,150 B2 * | 2/2008 | Coenen et al. | 493/418 |

(Continued)

FOREIGN PATENT DOCUMENTS

| | | |
|---|---|---|
| JP | 07-205943 | 8/1995 |
| JP | 2002-518097 A | 2/2002 |

(Continued)

OTHER PUBLICATIONS

International Search Report for corresponding International Application No. PCT/JP2010/000351 mailed Apr. 20, 2010.

*Primary Examiner* — Christopher Harmon
(74) *Attorney, Agent, or Firm* — Renner, Otto, Boisselle & Sklar, LLP (57) ABSTRACT

A method including: a step of carrying a continuous web; a cut-off step of cutting the continuous web into individual worn articles 1; a first folding step of folding the diaper body 2 so that a skin-contact surface of a front portion 20 and a skin-contact surface of a back portion 21 lie one each other; and a folding step of folding a pair of side panels 3, wherein in the folding step, the pair of side panels 3 are folded as second pads 32, which rotate in a folding direction in which the side panels 3 are folded with respect to a first pad 31, rotate in the folding direction, while the diaper body 2 is held on the first pad 31 and while the side panels 3 are held by the second pads 32.

8 Claims, 7 Drawing Sheets (56) References Cited

U.S. PATENT DOCUMENTS

| | | | | |
|---|---|---|---|---|
| 8,225,837 | B2* | 7/2012 | Schneider | 156/443 |
| 8,556,790 | B2* | 10/2013 | Fujita | 493/357 |
| 8,617,341 | B2* | 12/2013 | Schneider | 156/285 |
| 2007/0043331 | A1* | 2/2007 | Haruki et al. | 604/385.3 |
| 2007/0137011 | A1 | 6/2007 | Couillard et al. | |
| 2007/0142194 | A1* | 6/2007 | Coenen et al. | 493/405 |

FOREIGN PATENT DOCUMENTS

| | | |
|---|---|---|
| JP | 2002-532194 A | 10/2002 |
| JP | 2005/000296 | 1/2005 |
| WO | 99/65441 A1 | 12/1999 |
| WO | 00/37007 A1 | 6/2000 |
| WO | 2007/070113 A1 | 6/2007 |

* cited by examiner

METHOD FOR MANUFACTURING DISPOSABLE WORN ARTICLE, AND MANUFACTURING APPARATUS THEREFOR

TECHNICAL FIELD

The present invention relates to a method for manufacturing a disposable worn article and a manufacturing apparatus therefor.

BACKGROUND ART

The pants-type diaper worn as if the wearer were wearing pants, and the open-type diaper including a diaper body and side panels have been known in the art as disposable worn articles.

With the open-type diaper, the diaper body is placed on the crotch of the wearer, and then the side panels are secured to the diaper body, thus fitting the diaper body to the wearer. The open-type diaper, when worn, is firmly secured by touch fasteners, or the like, provided on the side panels, and therefore it is difficult to pull up or pull down the hip portion of the diaper body after it is worn, as opposed to a pants-type diaper.

In view of this, diaper manufacturing methods have been proposed in the art in which the side panels are tentatively attached to the diaper body in advance so that it can be used as if it were a pants-type so that the hip portion can be pulled up or pulled down after it is worn.

CITATION LIST

Patent Document

[FIRST PATENT DOCUMENT] Japanese National Phase PCT Laid-Open Publication No. 2002-532194 (Abstract)
[SECOND PATENT DOCUMENT] Japanese National Phase PCT Laid-Open Publication No. 2002-518097 (Abstract)

SUMMARY OF THE INVENTION

Technical Problem

The first patent document fails to disclose a method for folding a pair of side panels to tentatively attach the side panels to the diaper body.

On the other hand, with the manufacturing method of the second patent document, the side panels are folded and the side panels are tentatively attached to the diaper body by passing the diaper body through a folding machine having a pair of blades. However, the side panels may be folded misaligned due to positional misalignment of the side panels occurring while the side panels pass through the folding machine.

It is therefore an object of the present invention to provide a method for manufacturing a disposable worn article and a manufacturing apparatus therefor, with which side panels of a disposable worn article which is a so-called "open-type diaper" can be folded with high precision.

Solution to Problem

In order to achieve object set forth above, a method for manufacturing a disposable worn article of the present invention is a method for manufacturing a disposable worn article including: a diaper body including a front portion covering a front side of a wearer, a back portion covering a back side of the wearer, and a crotch portion between the front portion and the back portion; and a pair of side panels connecting the front portion and the back portion in a girth direction, the method comprising: a step of carrying a continuous web to be the disposable worn article in a longitudinal direction perpendicular to the girth direction; a severing step of severing the continuous web along a virtual first line extending in the girth direction so as to sever the continuous web into individual worn articles; a first folding step of folding the diaper body along a virtual second line extending in the girth direction so that a skin-contact surface of the front portion and a skin-contact surface of the back portion lie on each other; and a second folding step of folding the pair of side panels so that the pair of side panels lie on a non-skin-contact surface of the back portion or the front portion, wherein in the second folding step, while the diaper body is held on a first pad and while the side panels are held on second pads rotating in a folding direction in which the side panels are folded with respect to the first pad, the second pads rotate in the folding direction, thereby the pair of side panels being folded.

Advantageous Effects of Invention

According to the present invention, a pair of side panels are folded in the second folding step while the diaper body is held on the first pad and while the side panels are held by the second pads. Therefore, the side panels do not undergo positional misalignment from a predetermined position when folding the side panels, and therefore the side panels can be folded with high precision with respect to the diaper body.

DESCRIPTION OF EMBODIMENTS

The present invention may be directed to a method for manufacturing a disposable worn article including: a diaper body including a front portion covering a front side of a wearer, a back portion covering a back side of the wearer, and a crotch portion between the front portion and the back portion; and a pair of side panels connecting the front portion and the back portion in a girth direction, the method comprising: a step of carrying a continuous web to be the diaper body in a longitudinal direction perpendicular to the girth direction; a first fastening step of fastening first end portions of the pair of side panels in the girth direction to opposite end portions of one of the back portion and the front portion in the girth direction; a severing step of severing the continuous web with the side panels fastened thereto along a virtual first line extending in the girth direction so as to sever the continuous web into individual worn articles; a first folding step of folding the diaper body along a virtual second line extending in the girth direction so that a skin-contact surface of the front portion and a skin-contact surface of the back portion lie on each other; and a second folding step of folding the pair of side panels so that the pair of side panels lie on a non-skin-contact surface of another one of the back portion and the front portion, wherein in the second folding step, while the diaper body is held on a first pad and while the side panels are held on second pads rotating in a folding direction in which the side panels are folded with respect to the first pad, the second pads rotate in the folding direction, thereby the pair of side panels being folded.

In the present invention, it is preferred that touch fasteners, with which the side panels can be re-fastened to the diaper body, are provided on the non-skin-contact surface of another one of the back portion and the front portion and skin-contact surfaces of the side panels, and the side panels folded in the second folding step are fastened to the non-skin-contact surface of the other one of the back portion and the front portion in such a manner that the side panels can be re-fastened thereto.

In such an embodiment, by providing the touch fasteners, the side panels can be easily re-fastened to the diaper body in conformity to the shape of the body of the wearer.

On the other hand, an apparatus for manufacturing a disposable worn article of the present invention is an apparatus for manufacturing a disposable worn article in which a pair of side panels, connecting a front portion covering a front side of a wearer and a back portion covering a back side of the wearer with each other in a girth direction, is folded onto a diaper body including the front portion, the back portion, and the crotch portion between the front portion and the back portion, including: a drum rotating about a first rotation shaft along a predetermined axis direction for carrying the diaper body in a longitudinal direction perpendicular to the girth direction; a plurality of first pads provided on the drum each for holding the diaper body; a pair of second pads provided at opposite ends of the first pad in the axis direction, each second pad capable of rotating about a second rotation shaft extending in a tangential direction of the drum so as to open and close with respect to the first pad; holding means for holding the side panels on the second pads; and driving means for rotating the second pads so that the second pads lie on the first pad while the side panels are held on the second pads by the holding means.

With the manufacturing apparatus of the present invention, the side panels can be folded while the diaper body is held on the first pad provided on the drum and while the side panels are held on the second pads. Therefore, side panels of a so-called "open-type diaper" can be folded with high precision.

Embodiment 1

An embodiment of the present invention will now be described with reference to the drawings.

Figures 1A, 1B, 1C, 1D, 1E:
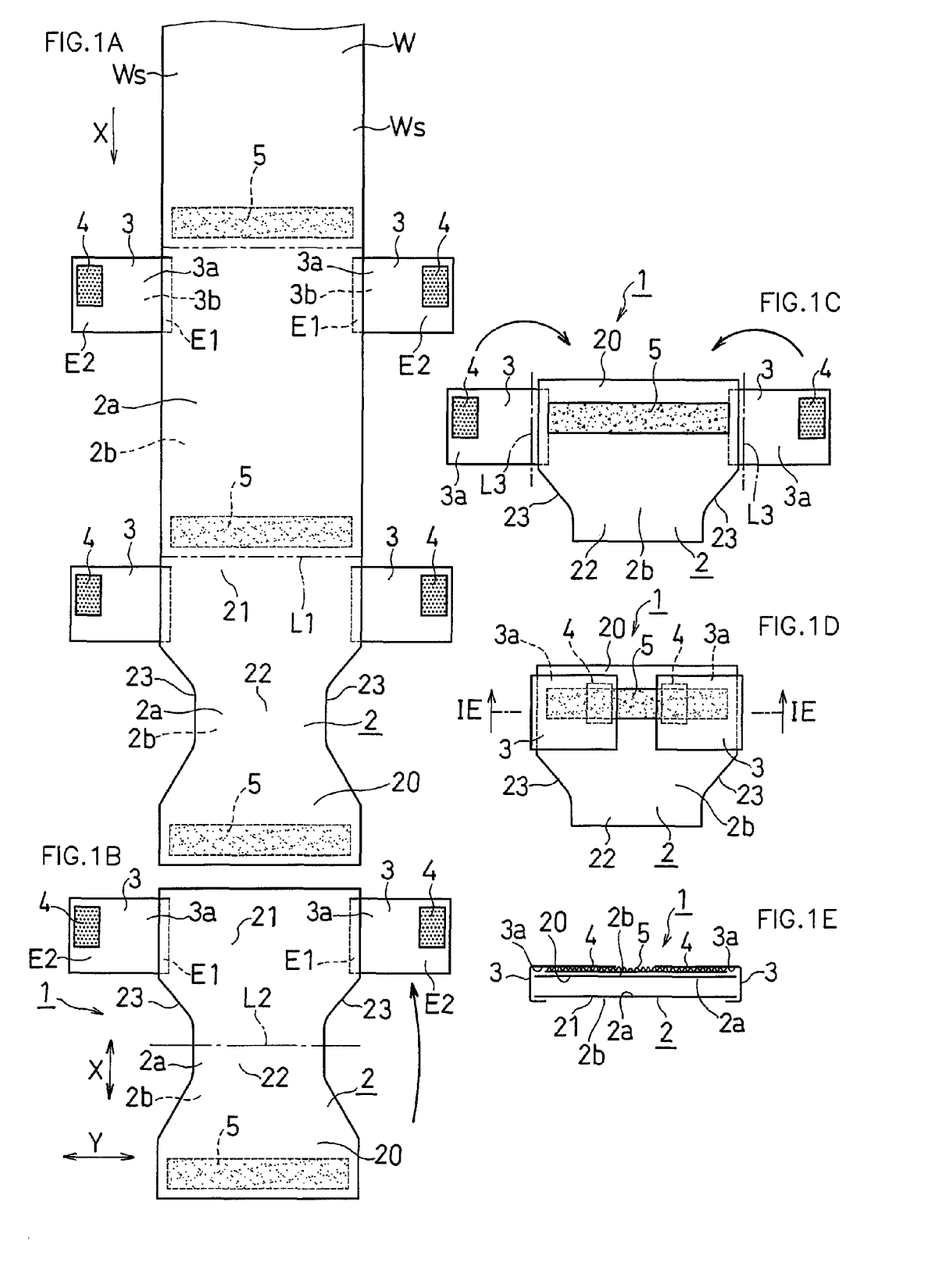
FIG. 1 shows schematic plan views and a cross-sectional view showing a method for manufacturing a diaper according to Embodiment 1 of the present invention.
Figure 2:
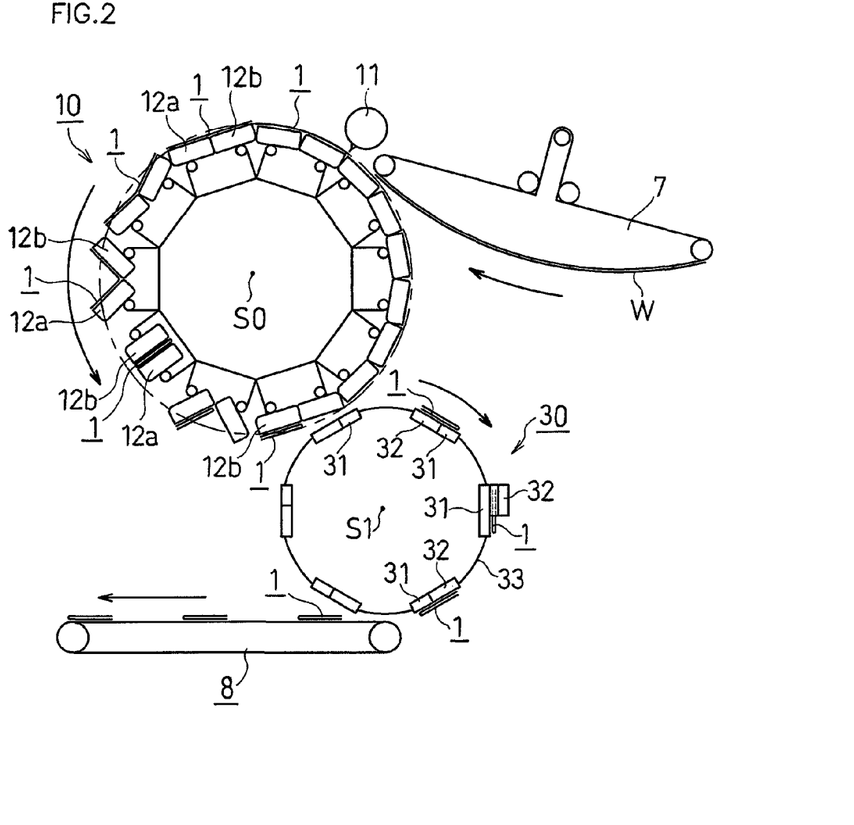
FIG. 2 is a schematic side view showing an apparatus for manufacturing the diaper.

FIGS. 1 and 2 show Embodiment 1.

Diaper 1:

As shown in FIG. 1B, the diaper 1 of Embodiment 1 includes a diaper body 2 and a pair of side panels 3. The diaper body 2 includes a front portion 20 covering the front side of the wearer, a back portion 21 covering the back side of the wearer, and a crotch portion 22 between the front portion 20 and the back portion 21.

First end portions (one end portions) E1 of the side panels 3 in a girth direction Y are fastened to the end portions of the back portion 21 of the diaper body 2 in the girth direction Y. The first end portions E1 of the side panels 3 on a skin-contact surface side 3a are fastened to a non-skin-contact surface 2b of the diaper body 2.

Male touch fasteners 4 are secured to second end portions (the other end portions) E2 of the side panels 3 in the girth direction Y on the skin-contact surface side 3a.

On the other hand, a female touch fastener 5 is provided on the non-skin-contact surface 2b of the front portion 20 of FIG. 1C. Note that in a case where the non-skin-contact surface 2b of the diaper body 2 is formed by a non-woven fabric, the non-woven fabric forms the female touch fastener 5.

An absorbent body (not shown) is provided on the diaper body 2.

Three-dimensional gathers may be provided on the diaper body 2.

The diaper body 2 may include around-leg portions 23 which are cut so as to conform to the legs of the wearer, and the around-leg portions 23 may include elastic members formed by rubber thread, or the like, for example, so as to conform to the legs of the wearer.

Moreover, an elastic member for fitting the diaper 1 to the wearer may be provided in portions of the front portion 20 and the back portion 21 of the diaper body 2 which are to be present around the torso. The elastic member may be, for example, a plurality of rubber threads or rubber tapes, a material including a film or a thermoplastic resin, or the like.

The crotch portion 22 of the diaper 1 is folded as shown in FIG. 1C along the virtual second line L2 shown in FIG. 1B so that the skin-contact surface 2a of the front portion 20 and the skin-contact surface 2a of the back portion 21 lie on each other. As shown in FIGS. 1D and 1E, the skin-contact surface side 3a of the side panel 3 of the diaper 1 is folded toward the female touch fastener 5 of the front portion 20 of the diaper body 2, and the diaper 1 is shipped with the pair of side panels 3 tentatively attached to the diaper body 2.

When wearing the diaper 1, a wearer can put it on as if it were a pants-type diaper, with the side panels 3 tentatively attached to the diaper body 2.

On the other hand, if the diaper 1 does not sufficiently fit to the wearer, the male touch fasteners 4 of the side panels 3 are once taken off the female touch fastener 5 of the diaper body 2, and the male touch fasteners 4 are re-attached to the female touch fastener 5 in conformity to the wearer, thereby fitting the diaper 1 to the wearer.

Manufacturing Apparatus:

Next, a manufacturing apparatus for manufacturing the folded diaper 1 shown in FIG. 1D will be described.

As shown in FIG. 2, this manufacturing apparatus includes a body folding apparatus 10, and a side panel folding apparatus 30.

The body folding apparatus 10 receives a continuous web W (FIG. 1A) which is carried, while being sucked, by a supply conveyer 7, cuts (severs) the continuous web W along the virtual first line L1 of FIG. 1A into individual diapers 1, and folds the diaper 1 as shown in FIG. 1C along the virtual second line L2 extending in the girth direction Y so that the skin-contact surface 2a of the front portion 20 and the skin-contact surface 2a of the back portion 21 of the diaper 1 shown in FIG. 1B lie on each other.

Body Folding Apparatus 10:

As shown in FIG. 2, the body folding apparatus 10 includes a rotating cutter 11 for cutting (severing) the continuous web W into individual diapers 1, and a plurality of pairs of suction pads 12a and 12b that rotate about the rotation center S0. The suction pads 12a and 12b hold the diaper 1 by the suction of air, for example, and the suction pads 12a and 12b are rotated as sets (pairs), each set including a pair of suction pads 12a and 12b.

The pair of suction pads 12a and 12b receives the diaper 1 in an open position, then moves into a (closed) position where the suction pads 12a and 12b are close to each other to fold the diaper body 2 (see FIG. 1C), moves into a position where the suction pads 12a and 12b are open while holding the diaper 1 on one suction pad 12b, and hands the diaper 1 held on the one suction pad 12b over to the side panel folding apparatus 30.

Note that the body folding apparatus 10 may be a folding apparatus described in Japanese Laid-Open Patent Publication No. 7-205943, for example.

Figure 3:
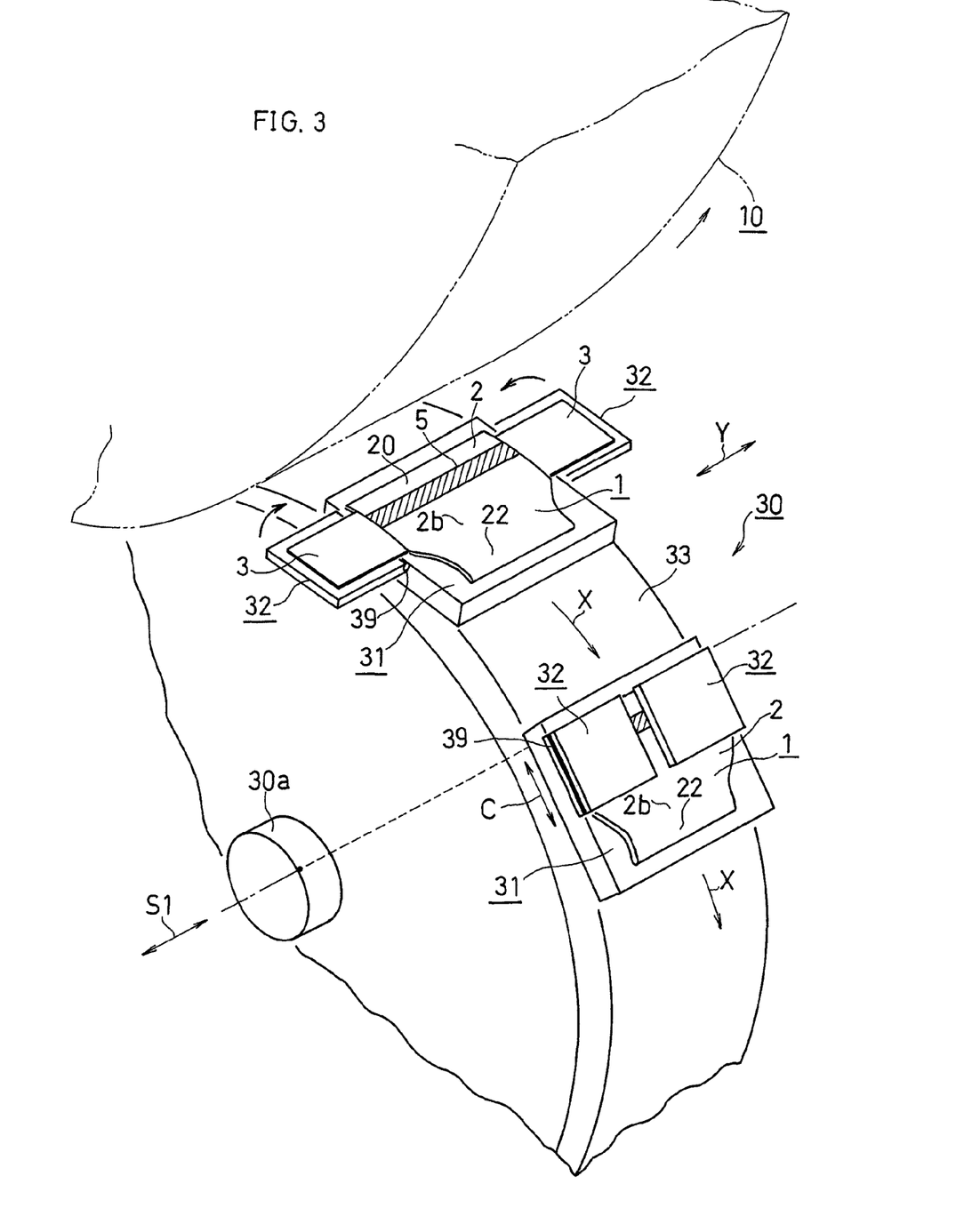
FIG. 3 is a schematic perspective view showing a side panel folding apparatus.

Side Panel Folding Apparatus 30:

As shown in FIG. 3, the side panel folding apparatus 30 includes a first pad 31, a pair of second pads 32, and a drum 33.

The drum 33 rotates about a first rotation shaft 30a along a predetermined axis S1 to carry the diapers 1 in the longitudinal direction (carrying direction) X perpendicular to the girth direction Y.

A plurality of first pads 31 are provided on the drum 33, each sucking and holding the diaper body 2 by the suction of air, for example.

The second pads 32 fold the pair of side panels 3 as indicated by arrows in FIG. 1C so that the pair of side panels 3 lie on the non-skin-contact surface 2b of the diaper body 2. The second pads 32 shown in FIG. 3 are provided on opposite ends of the first pad 31 in the axis direction S1, and are provided so that they can rotate about a second rotation shaft 39 extending in the tangential direction C of the drum 33.

As will be described later, the second pad 32 includes holding means for holding the side panel 3 on the second pad 32, and driving means for rotating the second pad 32 toward the first pad 31 so that the second pad 32 lies on the first pad 31 while the side panel 3 is held on the second pad 32 by the holding means.

Mechanism for Rotating Second Pad 32:

While the second pads 32 are provided on opposite end portions of the first pad 31 in the girth direction Y, one of the second pads 32 will be illustrated in the following description.

Figure 4:
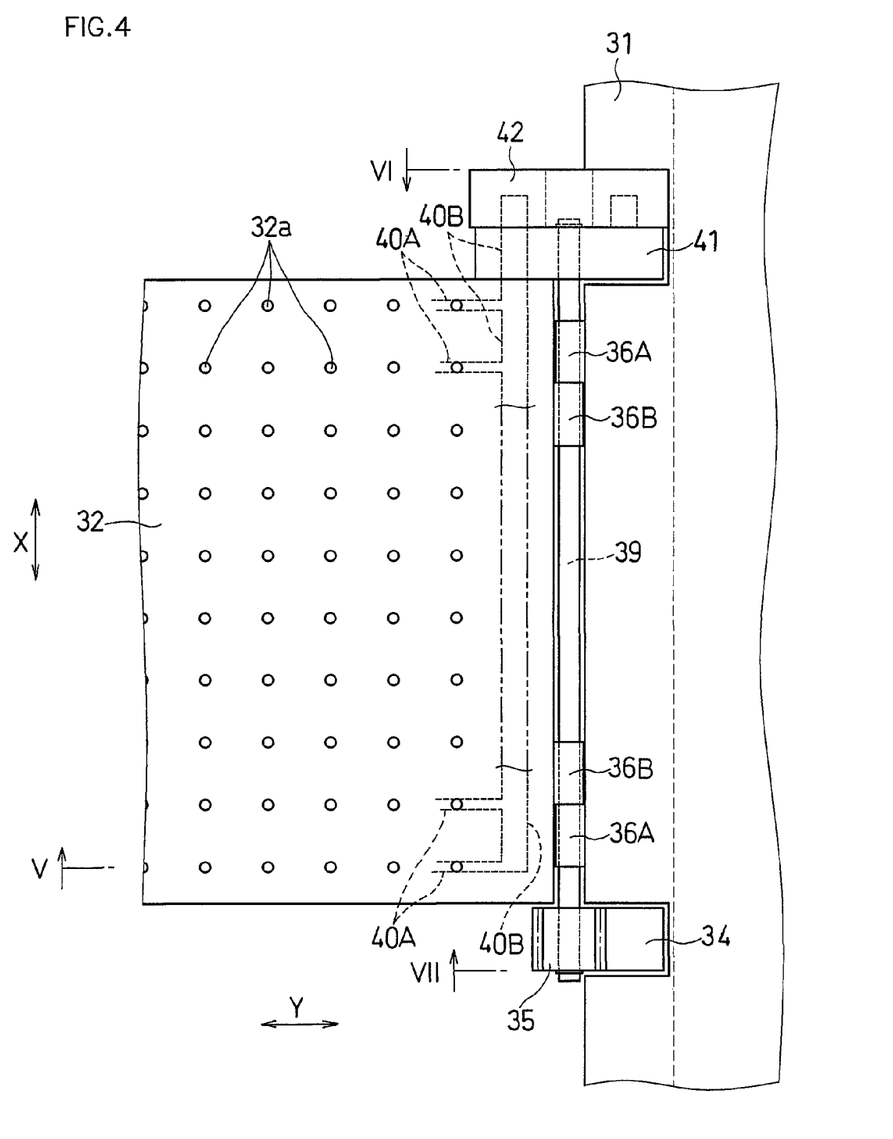
FIG. 4 is a schematic plan view showing a part of first and second pads.
Figure 5:
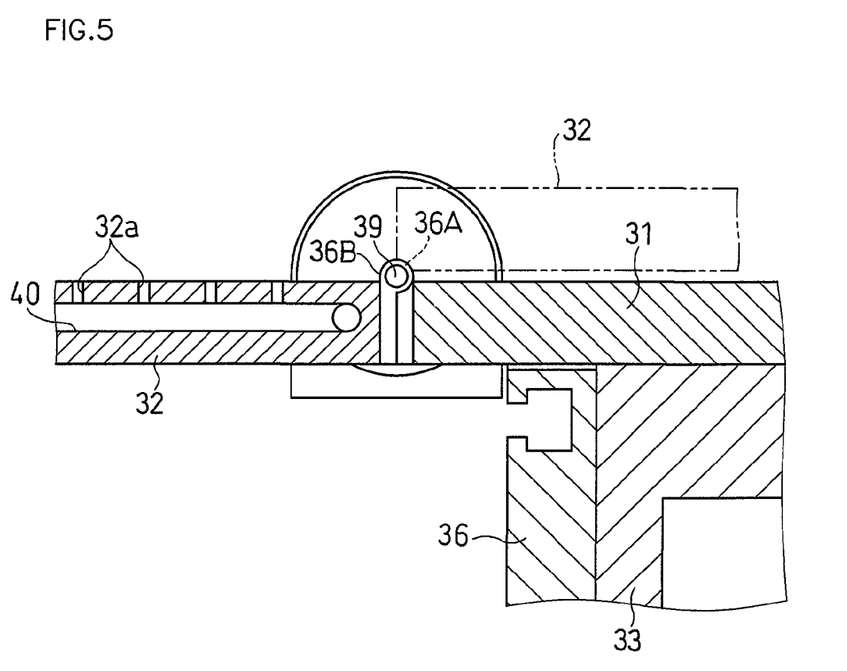
FIG. 5 is a schematic cross-sectional view taken along line V-V in FIG. 4, showing a mechanism for opening/closing a second pad.

As shown in FIGS. 4 and 5, the second pad 32 is provided rotatably with respect to the first pad 31 by means of hinges 36A and 36B and the second rotation shaft 39. Therefore, the second pad 32 can rotate from the open state indicated by a solid line in FIG. 5 to the closed state (folded state) indicated by a two-dot-chain line.

Holding Means:

As shown in FIG. 4, a plurality of air holes 32a shown in FIG. 4 are open in the upper surface of the second pad 32, i.e., the surface on which the second pad 32 in the open state of FIG. 3 receives the side panel 3 of the diaper 1 from the body folding apparatus 10. The air holes 32a communicate with a single communication tube 40B via a plurality of thin tubes 40A.

On the other hand, a rotating member 41 is provided at one of the end portions of the second pad 32 in the longitudinal direction X. The rotating member 41 is fixed to the second pad 32 and rotates about the second rotation shaft 39 together with the second pad 32. The communication tube 40B is provided continuous with the rotating member 41. A fixed member 42 fixed to the first pad 31 is in surface contact with the rotating member 41.

Figure 6A:
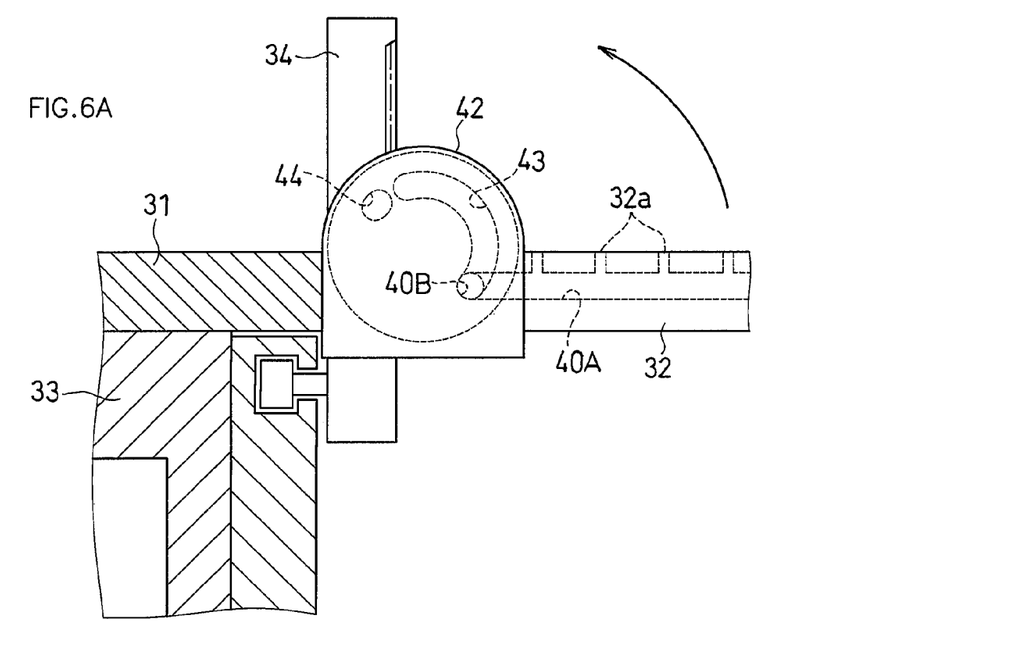
FIGS. 6A and 6B are schematic cross-sectional views taken along line VI-VI in FIG. 4, showing second pad holding means.

As shown in FIG. 6A, the fixed member 42 includes a negative pressure chamber 43 and a positive pressure chamber 44, and the negative pressure chamber 43 and the positive pressure chamber 44 communicate with an air pressure source (not shown). The air pressure source includes, for example, a pump, a tank, an ejector, and the like. As shown in FIG. 6A, if the end portion of the communication tube 40B of the rotating member 41 (FIG. 4) communicates with the negative pressure chamber 43, the air inside the communication tube 40B is sucked. On the other hand, as shown in FIG. 6B, if the end portion of the communication tube 40B communicates with the positive pressure chamber 44, a pressurized air is pressed into the communication tube 40B.

Figure 6B:
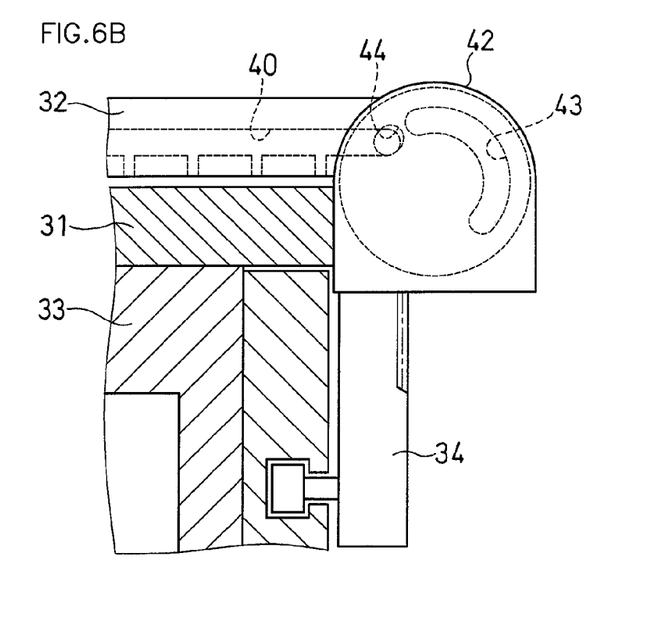

That is, the air is sucked through the air holes 32a via the communication tube 40B and the thin tube 40A, from the open state of the second pad 32 shown in FIG. 6A until the second pad 32 rotates to approach the closed state of the second pad 32 shown in FIG. 6B. Thus, the side panel 3 on the second pad 32 is sucked onto the second pad 32.

On the other hand, when the second pad 32 is rotated to the closed state, the air is blown out of the air holes 32a, thereby releasing the side panel 3, which has been sucked onto the second pad 32, from the second pad 32.

Thus, the air holes 32a, the thin tube 40A, the communication tube 40B, the fixed member 42 and the air pressure source together form the holding means for holding the side panel 3 on the second pad 32.

Note that a mechanism described in WO2002/070213 may be employed, for example, for the air suction and discharge mechanism.

Driving Means:

Driving means for rotating the second pad 32 with respect to the first pad 31 is provided at the other end portion of the second pad 32 in the longitudinal direction X shown in FIG. 4.

The hinge 36B on the second pad 32 side is fixed to the second rotation shaft 39, and a pinion 35 is fixed at the other end portion of the second rotation shaft 39.

Figure 7A:
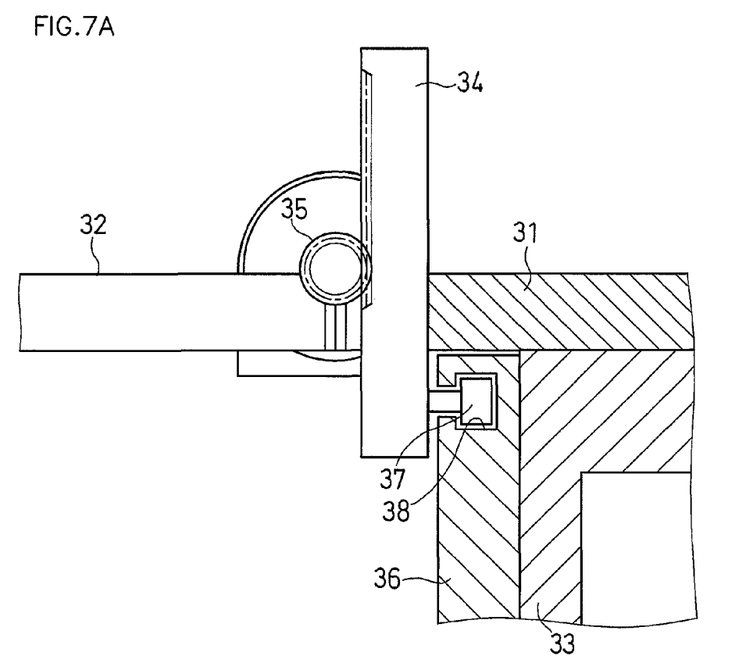
FIGS. 7A and 7B are schematic cross-sectional views taken along line VII-VII in FIG. 4, showing second pad driving means.
Figure 7B:
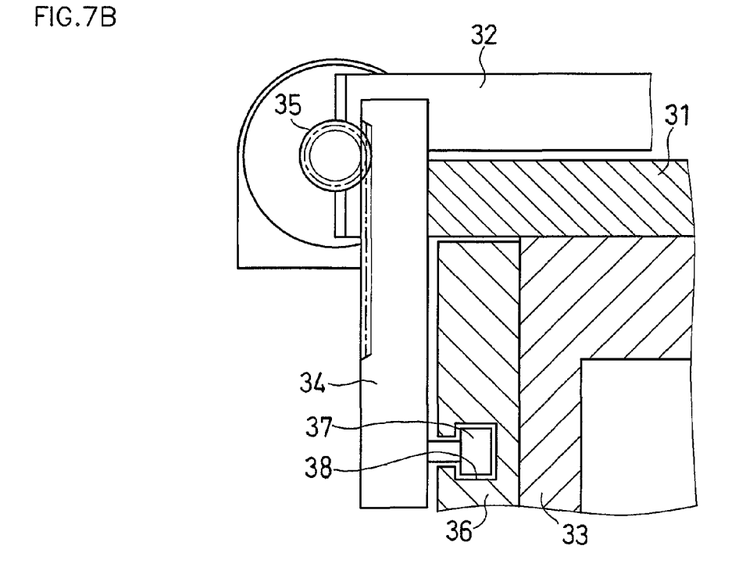

As shown in FIGS. 7A and 7B, a rack 34 meshes with the pinion 35. A cam follower 37 is provided in a lower portion of the rack 34, and a fixed plate 36 is provided on a side portion of the drum 33, the fixed plate 36 including a cam groove 38 formed therein along which the cam follower 37 is guided.

The first pad 31 is fixed to the drum 33, and the first pad 31 rotates following the rotation of the drum 33. On the other hand, the fixed plate 36 is fixed to a frame (not shown), and the cam follower 37 is guided along the cam groove 38 formed in the fixed plate 36 by the rotation of the drum 33. As the cam follower 37 is guided along the cam groove 38, the rack 34 reciprocates between the upper position shown in FIG. 7A and the lower position shown in FIG. 7B.

The up-down movement of the rack 34 rotates the pinion 35 which meshes with the rack 34, and rotates the second rotation shaft 39 which is fixed to the pinion 35. Thus, the second pad 32 is opened/closed via the hinge 36B fixed to the second rotation shaft 39 as shown in FIGS. 7A and 7B.

Thus, the rack 34, the pinion 35, the cam follower 37 and the cam groove 38 together form the driving means for rotating the second pad 32.

Next, a method for manufacturing the diaper 1 will be described.

Step of Carrying Continuous Web W:

As shown in FIG. 1A, the continuous web W to be the diaper body 2 is carried in the longitudinal direction X perpendicular to the girth direction Y. The continuous web W is, for example, a continuous laminated sheet, and the female touch fastener 5 is fastened (joined) to the non-skin-contact surface 2b of the front portion 20 of the diaper body 2. Absorbent bodies (not shown), etc., are placed intermittently on the continuous web W.

First Fastening Step:

Then, the first end portions E1 of pairs of side panels 3 in the girth direction Y are fastened (joined) at predetermined intervals to the opposite end portions Ws of portions of the continuous web W to be the back portions 21 of the diaper bodies 2. The side panels 3 may be welded to the opposite end portions Ws by thermal welding or sonic (ultrasonic bonding), or may be bonded to the opposite end portions Ws using an adhesive such as a hot-melt resin.

Cut-Off (Severing) Step:

The continuous web W with the side panels 3 fastened thereto is carried by the supply conveyer 7 shown in FIG. 2 onto the pair of suction pads 12a and 12b of the body folding apparatus 10, and is cut (severed) into individual diapers 1 by the rotating cutter 11. That is, as shown in FIG. 1A, the continuous web W is cut along the virtual first line L1 extending in the girth direction Y so as to be cut (severed) into individual diapers 1 as shown in FIG. 1B.

First Folding Step:

As shown in FIG. 2, the diaper 1 sucked and held on the suction pads 12a and 12b is folded as the suction pads 12a and 12b move toward a (closed) position where they are close to each other. That is, while being held by the suction pads 12a and 12b, the diaper body 2 is folded as shown in FIG. 1C along the virtual second line L2 extending in the girth direction Y so that the skin-contact surface 2a of the front portion 20 and the skin-contact surface 2a of the back portion 21 lie on each other as indicated by an arrow in FIG. 1B.

Thus, by folding the diaper body while sucking the diaper body, a misalignment due to the thickness of the crotch portion is unlikely to occur when the diaper is folded in two. That is, it is possible to fold the diaper body with high precision even though the thickness is large because the absorbent body, etc., are placed on the crotch portion.

As shown in FIG. 2, simultaneously with the folding, the air is discharged from one suction pad 12a, the suction pads 12a and 12b move away from each other, and the folded diaper 1 is held on the other suction pad 12b. Then, the diaper 1 on the other suction pad 12b is handed over to the first pad 31 and the second pad 32 of the side panel folding apparatus 30.

Second Folding Step:

As shown in FIG. 3, the diaper body 2 of the diaper 1 is sucked and held on the first pad 31 while the pair of side panels 3 are sucked and held on the second pads 32.

Then, as shown in FIGS. 7A and 7B, as the second pads 32 rotate toward the first pad 31, the side panels 3 are folded toward the diaper body 2 while the diaper body 2 is held on the first pad 31 and while the pair of side panels 3 are held by the second pads 32 and 32, as shown in FIG. 3.

With such a second folding step, the side panels 3 are folded as shown in FIG. 1D along the virtual third lines L3 shown in FIG. 1C. The pair of side panels 3 is folded so that the skin-contact surface side 3a lies on the non-skin-contact surface 2b of the front portion 20 of the diaper body 2.

As shown in FIGS. 1D and 1E, with such folding of the side panels 3, the male touch fasteners 4 of the side panels 3 engage with the female touch fastener 5 provided on the front portion 20 of the diaper body 2, and the side panels 3 are tentatively fastened to the front portion 20 of the diaper body 2 in such a manner that the side panels 3 can be re-fastened thereto.

After the tentative fastening, the air is discharged through the air holes 32a shown in FIG. 6B, and the side panels 3, which have been sucked onto the second pads 32, come off of the second pads 32. Then, the second pads 32 are rotated reversely into an open state shown in FIG. 6A. If the force of engagement of the fastener is sufficiently large, the side panels 3 can be allowed to engage with the front portion 20 and come off of the second pads 32, even without discharging the air. In such a case, it is not necessary to discharge the air.

After the second pads 32 are rotated to the open state, the diaper 1 on the first pad 31 is handed over to a carrying conveyer 8 and carried downstream as shown in FIG. 2.

Note that although Embodiment 1 has been described with respect to an example of the diaper 1 in which the side panels 3 are fastened (joined) to the diaper body 2, a diaper in which the side panels and the diaper body are formed integral with each other may be employed. In such a case, the first fastening step is not needed.

While preferred embodiments have been described above with reference to the drawings, obvious variations and modifications will readily occur to those skilled in the art upon reading the present specification.

For example, the side panels may be fastened to the front portion side of the diaper body.

While the first folding step and the second folding step are separately performed by the body folding apparatus 10 and the side panel folding apparatus 30 in the above description, the first and second folding steps may be performed with a single drum.

Moreover, as the driving means for rotating the second pads, the second pads may be driven by a motor, or various mechanisms such as a ball screw mechanism or a cylinder mechanism may be employed, for example, in addition to the mechanism using a cam, a rack and a pinion described above.

As the mechanism for holding the side panels on the second pads, the side panels may be held by a plurality of needles, or the side panels may be held by being sandwiched, for example, in addition to the method of sucking them by the air described above.

Thus, such variations and modifications shall fall within the scope of the present invention as defined by the appended claims.

INDUSTRIAL APPLICABILITY

The present invention is applicable to methods for manufacturing diapers and manufacturing apparatuses therefor.

DESCRIPTION OF THE REFERENCE NUMERALS

1: Diaper (an example of a disposable worn article)
2: Diaper body
2a: Skin-contact surface
2b: Non-skin-contact surface
3: Side panel
5: Female touch fastener
20: Front portion
21: Back portion
22: Crotch portion
31: First pad
32: Second pad
32a: Air holes (part of holding means)
33: Drum
34: Rack (part of driving means)
35: Pinion (part of driving means)
37: Cam follower (part of driving means)
38: Cam groove (part of driving means)
40A: Thin tube (part of holding means)

40B: Communication tube (part of holding means)
42: Fixed member (part of holding means)
E1: First end portion
L1: First line
L2: Second line
X: Longitudinal direction
Y: Girth direction

The invention claimed is:

1. A method for manufacturing a disposable worn article including: a diaper body including a front portion covering a front side of a wearer, a back portion covering a back side of the wearer, and a crotch portion between the front portion and the back portion; and a pair of side panels connecting the front portion and the back portion in a girth direction, the method comprising:
a step of carrying a continuous web to be the disposable worn article in a longitudinal direction perpendicular to the girth direction;
a severing step of severing the continuous web along a virtual first line extending in the girth direction so as to sever the continuous web into individual worn articles;
a first folding step of folding, by a body folding apparatus including a plurality of pairs of suction pads, the diaper body along a virtual second line extending in the girth direction so that a skin-contact surface of the front portion and a skin-contact surface of the back portion lie on each other; and
a second folding step of folding, by a side panel folding apparatus, the pair of side panels so that the pair of side panels of the diaper body handed over from the body folding apparatus lie on a non-skin-contact surface of the back portion or the front portion,
wherein in the second folding step, while the diaper body is held on a first pad and while the side panels are held on second pads rotating in a folding direction in which the side panels are folded with respect to the first pad, the second pads rotate in the folding direction toward the first pad so that the second pads lie on the first pad, thereby the pair of side panels being folded.

2. The method for manufacturing a worn article according to claim 1, further comprising:
a first fastening step of fastening first end portions of the pair of side panels in the girth direction to opposite end portions of one of the back portion and the front portion in the girth direction, wherein
in the severing step, severing the continuous web with the side panels fastened thereto along a virtual first line extending in the girth direction so as to sever the continuous web into individual worn articles; and
in the second folding step, folding, by the side panel folding apparatus, the pair of side panels of the handed-over diaper body so that the pair of side panels lie on a non-skin-contact surface of another one of the back portion and the front portion.

3. The method for manufacturing a worn article according to claim 2, wherein touch fasteners, with which the side panels are refastenable to the diaper body, are provided on the non-skin-contact surface of the other one of the back portion and the front portion and skin-contact surfaces of the side panels, and the side panels folded in the second folding step are fastened to the non-skin-contact surface of the other one of the back portion and the front portion in such a manner that the side panels are refastenable thereto.

4. An apparatus for manufacturing a disposable worn article in which a pair of side panels, connecting a front portion covering a front side of a wearer and a back portion covering a back side of the wearer in a girth direction, is folded onto a diaper body including the front portion, the back portion, and the crotch portion between the front portion and the back portion, the apparatus comprising:
a body folding apparatus including a plurality of pairs of suction pads that fold the diaper body by moving from an open position to a closed position, the plurality of suction pads rotating about a rotation center; and
a side panel folding apparatus including a first pad and a pair of second pads, wherein the diaper body is configured to be held on one of the pair of suction pads of the body folding apparatus on one of the pair of suction pads of the body folding apparatus is handed over to the first pad after the folding the diaper body, the side panel folding apparatus comprising:
a drum rotating about a first rotation shaft along a predetermined axis direction for carrying the diaper body in a longitudinal direction perpendicular to the girth direction;
a plurality of the first pads provided on the drum each for holding the diaper body;
a pair of the second pads provided at opposite ends of the first pad in the axis direction, each second pad capable of rotating about a second rotation shaft extending in a tangential direction of the drum so as to open and close with respect to the first pad so that the second pads lie on the first pad;
holding means for holding the side panels on the second pads; and
driving means for rotating the second pads so that the second pads lie on the first pad while the side panels are held on the second pads by the holding means.

5. A method for manufacturing a disposable worn article including: a diaper body including a front portion covering a front side of a wearer, a back portion covering a back side of the wearer, and a crotch portion between the front portion and the back portion; and a pair of side panels connecting the front portion and the back portion in a girth direction, the method comprising:
a step of carrying a continuous web to be the disposable worn article in a longitudinal direction perpendicular to the girth direction;
a severing step of severing the continuous web along a virtual first line extending in the girth direction so as to sever the continuous web into individual worn articles;
a first folding step of folding, by a body folding apparatus, the diaper body along a virtual second line extending in the girth direction so that a skin-contact surface of the front portion and a skin-contact surface of the back portion lie on each other,
the body folding apparatus including a rotating cutter for severing the continuous web into individual diapers, and a plurality of pairs of suction pads that rotate about the rotation center,
in the first folding step, the pair of suction pads receiving the diaper in an open position, then moving into a closed position where the suction pads are close to each other to fold the diaper body, moving into a position where the suction pads are open while holding the diaper on one suction pad; and
a second folding step of folding, by a side panel folding apparatus, the pair of side panels so that the pair of side panels of the diaper handed over from the body folding apparatus to the side panel folding apparatus lie on a non-skin-contact surface of the back portion or the front portion,
the side panel folding apparatus including a first pad, a pair of second pads, and a drum, a plurality of the first pads being provided on the drum, the second pads being provided on opposite ends of the first pad, in the axis direction, and being provided so that they can rotate about a second rotation shaft extending in the tangential direction of the drum, wherein in the second folding step, while the diaper body is held on the first pad and while the side panels are held on second pads rotating in a folding direction in which the side panels are folded with respect to the first pad, the second pads rotate in the folding direction toward the first pad so that the second pads lie on the first pad, thereby the pair of side panels being folded.

6. The method for manufacturing a worn article according to claim 5, further comprising:

a first fastening step of fastening first end portions of the pair of side panels in the girth direction to opposite end portions of one of the back portion and the front portion in the girth direction, wherein in the severing step, severing the continuous web with the side panels fastened thereto along a virtual first line extending in the girth direction so as to sever the continuous web into individual worn articles; and in the second folding step, by the side panel folding apparatus, the pair of side panels of the handed-over diaper body so that the pair of side panels lie on a non-skin-contact surface of another one of the back portion and the front portion.

7. The method for manufacturing a worn article according to claim 6, wherein touch fasteners, with which the side panels are refastenable to the diaper body, are provided on the non-skin-contact surface of the other one of the back portion and the front portion and skin-contact surfaces of the side panels, and the side panels folded in the second folding step are fastened to the non-skin-contact surface of the other one of the back portion and the front portion in such a manner that the side panels are refastenable thereto.

8. An apparatus for manufacturing a disposable worn article in which a pair of side panels, connecting a front portion covering a front side of a wearer and a back portion covering a back side of the wearer in a girth direction, is folded onto a diaper body including the front portion, the back portion, and the crotch portion between the front portion and the back portion, the apparatus comprising:

a body folding apparatus including a rotating cutter for severing the continuous web into individual diapers, and a plurality of pairs of suction pads that fold the diaper body by moving from an open position to a closed position, the plurality of suction pads rotating about a rotation center, in folding the diaper body, the pair of suction pads receiving the diaper in the open position, then moving into the closed position where the suction pads are close to each other to fold the diaper body, moving into a position where the suction pads are open while holding the diaper on one suction pad; and a side panel folding apparatus including a first pad, a pair of second pads, and a drum, wherein the diaper body is configured to be held on one of the pair of suction pads of the body folding apparatus is handed over to the first pad after the folding the diaper body, the side panel folding apparatus comprising:

the drum rotating about a first rotation shaft along a predetermined axis direction for carrying the diaper body in a longitudinal direction perpendicular to the girth direction;

a plurality of the first pads provided on the drum each for holding the diaper body;

a pair of the second pads provided at opposite ends of the first pad in the axis direction, each second pad capable of rotating about a second rotation shaft extending in a tangential direction of the drum so as to open and close with respect to the first pad so that the second pads lie on the first pad;

holding means for holding the side panels on the second pads; and driving means for rotating the second pads so that the second pads lie on the first pad while the side panels are held on the second pads by the holding means.

\* \* \* \* \*